US009826989B2

(12) United States Patent
Chu

(10) Patent No.: US 9,826,989 B2
(45) Date of Patent: Nov. 28, 2017

(54) DRILLING DEVICE FOR ACROMIOPLASTY

(71) Applicant: Eui Tak Chu, Seoul (KR)

(72) Inventor: Eui Tak Chu, Seoul (KR)

(73) Assignee: Eui Tak Chu, Seoul (KR)

(*) Notice: Subject to any disclaimer, the term of this patent is extended or adjusted under 35 U.S.C. 154(b) by 414 days.

(21) Appl. No.: 14/497,368

(22) Filed: Sep. 26, 2014

(65) Prior Publication Data

US 2015/0094726 A1    Apr. 2, 2015

(30) Foreign Application Priority Data

Sep. 27, 2013  (KR) .................. 10-2013-0114956

(51) Int. Cl.
*A61B 17/16* (2006.01)

(52) U.S. Cl.
CPC ...... *A61B 17/1684* (2013.01); *A61B 17/1624* (2013.01); *A61B 17/1633* (2013.01); *A61B 17/1644* (2013.01)

(58) Field of Classification Search
CPC . A61B 17/16; A61B 17/1622–17/1633; A61B 17/1637; A61B 17/1644; A61B 17/1655; A61B 17/1657; A61B 17/1662; A61B 17/1684; B23Q 5/045
USPC .......................... 606/80, 167, 170, 179, 180
See application file for complete search history.

(56) References Cited

U.S. PATENT DOCUMENTS

| | | | | | |
|---|---|---|---|---|---|
| 2,262,706 | A | * | 11/1941 | Benda | B23B 45/00 74/417 |
| 2,617,455 | A | * | 11/1952 | Kuta | B27C 3/08 173/165 |
| 2,669,162 | A | * | 2/1954 | Arliss | B23Q 5/045 409/144 |
| 5,041,119 | A | * | 8/1991 | Frigg | A61B 17/1703 606/79 |
| 5,052,496 | A | * | 10/1991 | Albert | B25F 3/00 173/164 |
| 5,219,174 | A | * | 6/1993 | Zurbrugg | A61B 17/162 279/158 |

(Continued)

*Primary Examiner* — Eric S Gibson
(74) *Attorney, Agent, or Firm* — Nixon Peabody LLP; David S. Resnick; David F. Crosby

(57) ABSTRACT

Provided is a drilling device for acromioplasty including an outer tube assembly including including a head section having a rotor having a first power transmission unit having a hollow structure and configured to receive power and a twist drill coupled to a lower end of the rotor with a hollow structure and provided with a suction port formed on an outer circumferential surface thereof, and an outer tube having a tubular shape and having one end to which the head section is coupled, an inner tube assembly including an inner tube having a hollow structure and rotatably inserted into the outer tube assembly, a second power transmission unit having a hollow structure and formed at one end of the inner tube to transmit power to the first power transmission unit, a rotation transmission unit formed at the other end of the inner tube and configured to receive a rotational force from the outside, and a discharge section disposed between the rotation transmission unit and the inner tube to discharge ground bone wastes to the outside, and a connecting pipe configured to connect the twist drill and the inner tube such that the ground bone wastes is discharged to the outside.

5 Claims, 4 Drawing Sheets

(56) References Cited

U.S. PATENT DOCUMENTS

| | | | | |
|---|---|---|---|---|
| 5,531,596 | A * | 7/1996 | Melde | A61C 1/052 433/104 |
| 5,540,708 | A * | 7/1996 | Lim | A61B 17/32002 30/240 |
| 5,863,159 | A * | 1/1999 | Lasko | B23Q 5/045 279/143 |
| 5,927,976 | A * | 7/1999 | Wu | A61C 19/08 433/80 |
| 6,152,941 | A * | 11/2000 | Himes | A61M 1/0043 604/22 |
| 6,352,127 | B1 * | 3/2002 | Yorde | B23Q 5/045 173/216 |
| 6,463,824 | B1 * | 10/2002 | Prell | B23Q 5/045 173/29 |
| 6,517,544 | B1 * | 2/2003 | Michelson | A61B 17/1659 606/80 |
| 6,610,059 | B1 * | 8/2003 | West, Jr. | A61B 17/32002 606/41 |
| 7,828,804 | B2 * | 11/2010 | Li | A61B 17/1617 408/156 |
| RE44,883 | E * | 5/2014 | Cha | A61B 17/1671 606/80 |
| 8,715,287 | B2 * | 5/2014 | Miller | A61B 10/025 606/80 |
| 2003/0078586 | A1 * | 4/2003 | Shapira | A61B 10/025 606/80 |
| 2003/0163136 | A1 * | 8/2003 | Joist | A61B 17/1644 606/80 |
| 2004/0181251 | A1 * | 9/2004 | Hacker | A61B 17/32002 606/170 |
| 2004/0230211 | A1 * | 11/2004 | Moutafis | A61B 17/320758 606/167 |
| 2005/0054972 | A1 * | 3/2005 | Adams | A61B 17/1688 604/22 |
| 2005/0177168 | A1 * | 8/2005 | Brunnett | A61B 17/1624 606/80 |
| 2005/0203527 | A1 * | 9/2005 | Carrison | A61B 17/1604 606/80 |
| 2005/0234477 | A1 * | 10/2005 | Brown | A61B 17/54 606/131 |
| 2006/0142775 | A1 * | 6/2006 | Heneberry | A61B 17/1633 606/80 |
| 2006/0217751 | A1 * | 9/2006 | O'Quinn | A61B 17/32002 606/180 |
| 2007/0010823 | A1 * | 1/2007 | Kucklick | A61B 17/32002 606/80 |
| 2007/0060936 | A1 * | 3/2007 | Benavitz | A61B 17/1633 606/180 |
| 2007/0118135 | A1 * | 5/2007 | Mansmann | A61B 17/16 606/80 |
| 2007/0282344 | A1 * | 12/2007 | Yedlicka | A61B 17/1615 606/80 |
| 2008/0003070 | A1 * | 1/2008 | Hor | B25F 5/001 408/124 |
| 2009/0023988 | A1 * | 1/2009 | Korner | A61B 17/1624 600/106 |
| 2009/0306669 | A1 * | 12/2009 | Takahashi | A61C 1/0076 606/80 |
| 2010/0057087 | A1 * | 3/2010 | Cha | A61B 17/1633 606/80 |
| 2010/0100098 | A1 * | 4/2010 | Norton | A61B 17/1631 606/80 |
| 2011/0004215 | A1 * | 1/2011 | Bradley | A61B 17/1684 606/84 |
| 2012/0109134 | A1 * | 5/2012 | Forsell | A61F 2/3603 606/80 |
| 2012/0116526 | A1 * | 5/2012 | Forsell | A61F 2/3603 623/22.11 |
| 2012/0203230 | A1 * | 8/2012 | Adams | A61B 17/32002 606/80 |
| 2013/0197552 | A1 * | 8/2013 | O'Brien, II | A61B 17/32002 606/170 |
| 2014/0276845 | A1 * | 9/2014 | Sharkey | A61F 2/461 606/80 |
| 2015/0094726 | A1 * | 4/2015 | Chu | A61B 17/1684 606/80 |
| 2016/0051267 | A1 * | 2/2016 | Sander | A61B 17/1682 606/80 |

* cited by examiner

DRILLING DEVICE FOR ACROMIOPLASTY

CROSS-REFERENCE TO RELATED APPLICATION

This application claims priority to and the benefit of Korean Patent Application No. 10-2013-0114956, filed on Sep. 27, 2013, the disclosure of which is incorporated herein by reference in its entirety.

BACKGROUND

1. Field of the Invention

The present invention relates to a drilling device for acromioplasty, and more particularly, to a preliminary drilling device for acromioplasty capable of allowing a surgeon to more accurately and easily remove bony spurs growing from anterior undersurface of acromion impinging with the humeral head upon acromioplasty by previously drilling the anterior undersurface of acromion by a depth of the anterior undersurface of the acromion, which is to be removed before acromioplasty, and supplementing immature experiences or mistakes of a surgeon who performs acromioplasty.

2. Discussion of Related Art

One of symptoms, which frequently appear in relation with shoulders of people in forties to fifties, is a subacromial impingement syndrome of a shoulder. While the subacromial impingement syndrome is similar to a frozen shoulder, which is widely known to many people, causes and treatments thereof are largely different.

The subacromial impingement syndrome of the shoulder is a disease that causes pains due to impingement with the rotator cuffs between the acromion and the humeral head whenever the shoulder is moved since a gap between the acromion of the bulging scapula which covers the shoulder like eaves and the humeral head is narrowed.

While the gap between the acromion and the humeral head is sufficient when he/she is young or has healthy shoulder joints, when the shoulder is repeatedly used for a sports activity with a large amount of shoulder movement such as golf, tennis, or the like, inflammation or tear may occur from the tendon due to growing of the bony spurs from the anterior undersurface of acromion and impingement with the humeral head. Since the sports activity is popularized in recent times, the subacromial impingement syndrome due to the sports activity frequently occurs as a cause of shoulder pains. In addition, as population of the aged is increased due to aging processes caused by extended life expectancy, a bone may grow from the anterior undersurface of acromion due to the aging.

Most of people endure the pains or delay the treatment when the shoulder pains occur. However, when the subacromial impingement syndrome is neglected without early treatment, the rotator cuffs are continuously worn due to the repeated impingement, and thus, probability of generating the rotator cuffs tear, in which the tendon is torn, is increased.

When the rotator cuffs are torn, pains radiate to the arm and/or the neck. While the pains are felt initially when the arms and shoulders move, the pains may occur regardless of movement when severe. In addition, raising the arm or rotating an arm shoulder also becomes difficult and stiff gradually, and then, the pains may be too severe to go to sleep.

If the rotator cuffs are not ruptured through the full thickness, conservative treatment or rehabilitation such as medications and physical therapy instead of a surgery is possible. However, when the symptoms are not improved for the better with the conservative treatment, surgical treatment should be considered. If the symptom is neglected, complications such as rotator cuffs tear or the like may occur. In order to prevent and completely treat the complications, acromioplasty using an arthroscope is performed to trim the bony spurs growing from the undersurface of acromion that impinges with the rotator cuffs, thereby preventing repeated impingement.

In order to perform the acromioplasty, the bony spurs growing from the anterior undersurface of acromion should be measured through radiography and/or MRI before the surgery to determine a depth to be removed, and the bony spurs should be removed to the measured depth through the acromioplasty in reality.

However, in performing the acromioplasty in reality, accurately removing the bony spurs to the desired depth determined through the radiography is difficult for even a surgeon who has much experience due to interferences of visualization such as bone debris, bleeding, soft tissues, or the like, in an operation field. In particular, it is further difficult for a unskillful surgeon with little experience in acromioplasty to perform the acromioplasty.

In addition, when the bony spurs and/or the bone of the anterior undersurface of acromion is overcorrected during the acromioplasty, the acromion may be fractured later or may not properly perform a function of a skeleton. On the other hand, when the bony spurs and/or the bone of the anterior undersurface of acromion is undercorrected, the subacromial impingement syndrome may be remained or may easily have a recurrence. For this reason, an apparatus for preventing undercorrection or overcorrection during the acromioplasty, more precisely measuring a depth and an amount of bones of the anterior undersurface of acromion to be removed, and performing the acromioplasty is needed, which is very helpful and makes the acromioplasty easier.

SUMMARY OF THE INVENTION

The present invention is directed to provide a drilling device for acromioplasty capable of allowing a surgeon to more accurately remove bony spurs growing from the anterior undersurface of acromion to an extent desired by the surgeon upon acromioplasty by previously drilling the anterior undersurface of acromion by a depth of the acromion, which is to be removed before acromioplasty, and in particular, supplementing immature experiences of a surgeon with little experience in acromioplasty.

An object of the present invention is not limited to the above-mentioned object, and additional objects will be apparent to those skilled in the art from the following description.

According to an aspect of the present invention to perform the technical aspect, there is provided a drilling device for acromioplasty including: an outer tube assembly including a head section that has a rotor having a first power transmission unit having a hollow structure and configured to receive power and a twist drill coupled to a lower end of the rotor with a hollow structure and provided with a suction port formed on an outer circumferential surface thereof, and an outer tube having a tubular shape and having one end to which the head section is coupled; an inner tube assembly including an inner tube having a hollow structure and rotatably inserted into the outer tube assembly, a second power transmission unit having a hollow structure and formed at one end of the inner tube to transmit power to the first power transmission unit, a rotation transmission unit formed at the other end of the inner tube and configured to receive a rotational force from the outside, and a discharge section disposed between the rotation transmission unit and the inner tube and including a discharge port configured to discharge ground bone wastes to the outside; and a connecting pipe configured to connect the twist drill and the inner tube such that the ground bone wastes introduced through the suction port is discharged to the outside through the inner tube.

According to another aspect of the present invention to perform the technical aspect, at least one gradation may be formed on the outer circumferential surface of the twist drill.

According to another aspect of the present invention to perform the technical aspect, the first power transmission unit and the second power transmission unit may transmit power using bevel gears.

According to another aspect of the present invention to perform the technical aspect, the inner tube assembly may be coupled to the outer tube assembly to expose the discharge section and the rotation transmission unit, and the outer tube assembly may include a coupling section formed at one side of the outer circumferential surface and configured to couple a hand piece connected to the discharge section and the rotation transmission unit to supply a rotational force to the rotation transmission unit while supplying air for suctioning the ground bone wastes discharged from the discharge section.

According to another aspect of the present invention to perform the technical aspect, the coupling section may include an elastic section formed at one side of the outer circumferential surface of the outer tube assembly, a push section disposed at a center of the elastic section, and a protrusion protruding from an end of the elastic section.

According to another aspect of the present invention to perform the technical aspect, an insertion section having a conical shape with a round end may be formed at one surface of the head section.

BRIEF DESCRIPTION OF THE DRAWINGS

The above and other objects, features, and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
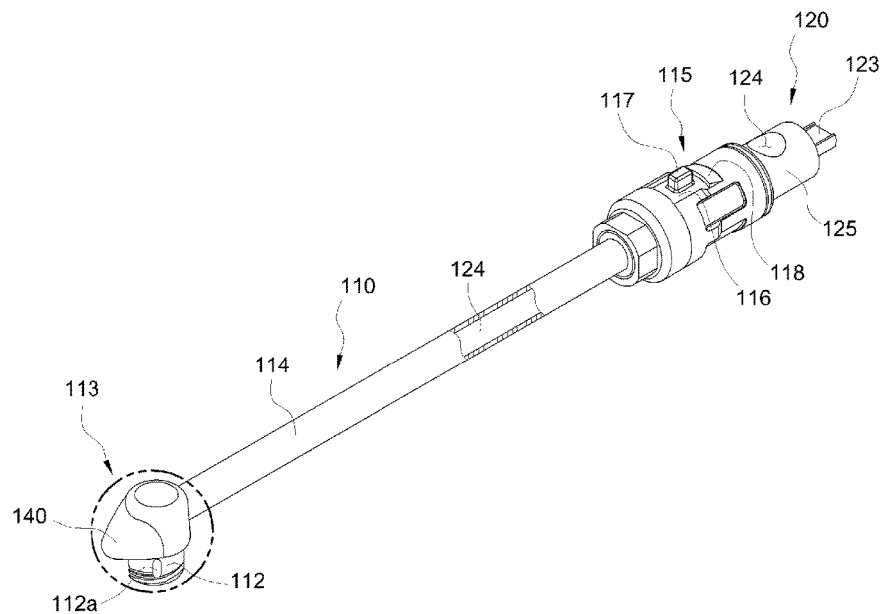
FIG. 1 is a perspective view of a drilling device for acromioplasty according to an embodiment of the present invention.

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention. Throughout the specification, the same components are designated by the same reference numerals. Meanwhile, terms used herein are provided for explaining embodiments of the present invention, not limiting the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated components, operations, motions, and/or devices, but do not preclude the presence or addition of one or more other components, operations, motions, and/or devices thereof.

Hereinafter, a drilling device for acromioplasty according to an embodiment of the present invention will be described in detail with reference to FIGS. 1 to 5B.

Figure 2:
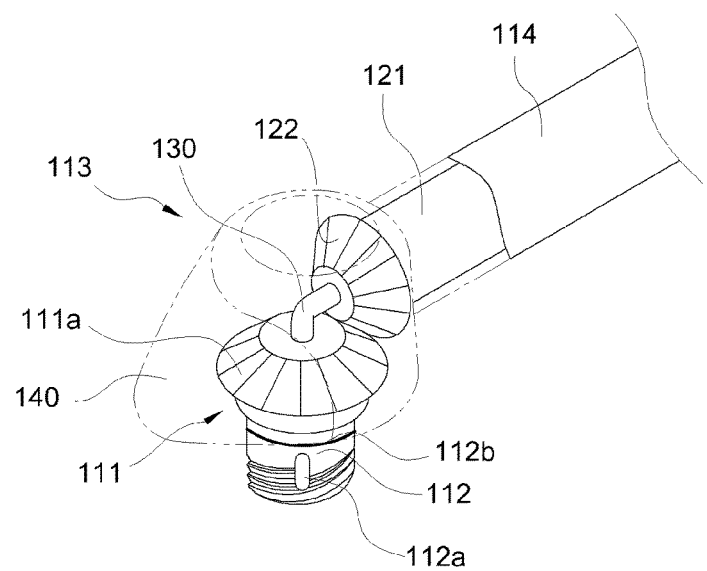
FIG. 2 is a view showing a head section.
Figure 3:
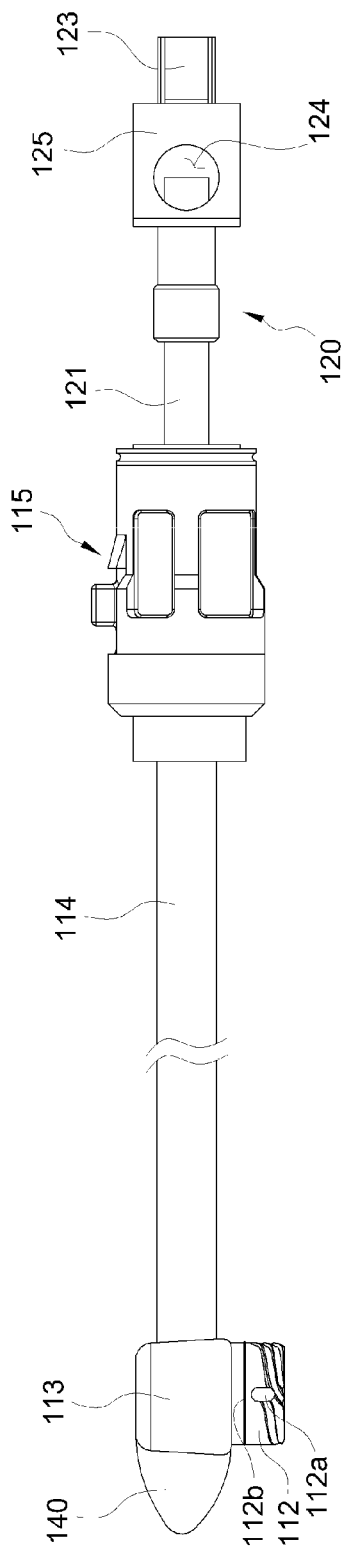
FIG. 3 is a side view of the drilling device for acromioplasty according to the embodiment of the present invention.

FIG. 1 is a perspective view of a drilling device for acromioplasty according to an embodiment of the present invention, FIG. 2 is a view showing a head section, and FIG. 3 is a side view of the drilling device for acromioplasty according to the embodiment of the present invention.

Referring to FIG. 1, a drilling device for acromioplasty 100 generally includes an outer tube assembly 110 and an inner tube assembly 120.

As shown in FIGS. 1 and 2, the outer tube assembly 110 includes a head section 113 that has a rotor 111 having a first power transmission unit 111a having a hollow structure and configured to receive power from an upper portion (a second power transmission unit 122) and a twist drill 112 coupled to a lower end of the rotor 111 with a hollow structure and provided with a suction port 112a formed on an outer circumferential surface thereof, and an outer tube 114 having a tubular shape and provided with one end to which the head section 113 is coupled.

The rotor 111 is coupled to a lower surface of the head section 113 to be rotated in an axial direction, and functions to transmit power such that the twist drill 112 can drill an acromion area.

The twist drill 112 is coupled to the lower end of the rotor 111, the rotor 111 and the twist drill 112 have hollow structures to be coupled to be connected to each other, the acromion area is drilled according to rotation of the rotor 111, and bone wastes ground at this time are suctioned through the suction port 112a formed on an outer circumferential surface of the twist drill 112.

At least one gradation 112b is formed on the outer circumferential surface of the twist drill 112 such that the drilled depth can be accurately measured during the surgery. When a plurality of gradations 112b are formed on the outer circumferential surface of the twist drill 112 at predetermined intervals, a surgeon can easily check whether the drilling is performed to a desired depth through the plurality of gradations.

It is most difficult for the surgeon who performs the acromioplasty to determine the extent of which the bony spurs should be precisely cut through the surgery. This is because the acromion cannot perform the function of a skeleton when the bony spurs of the acromion is overcorrected, and the subacromial impingement syndrome is remained or may easily recur when the bony spurs of the acromion is undercorrected.

As shown in FIGS. 1 to 3, the inner tube assembly 120 includes an inner tube 121 having a hollow structure and rotatably inserted into the outer tube assembly 110, the second power transmission unit 122 having a hollow structure formed at one end of the inner tube 121 and configured to transmit power to the first power transmission unit 111a, a rotation transmission unit 123 formed at the other end of the inner tube 121 and configured to receive a rotational force from the outside, and a discharge section 125 disposed between the rotation transmission unit 123 and the inner tube 121 and including a discharge port 124 configured to discharge the ground bone wastes to the outside.

Here, the first power transmission unit 111a and the second power transmission unit 122 may be configured to transmit power using bevel gears as shown in FIG. 2. While the embodiment exemplifies that the first power transmission unit 111a is disposed perpendicular to the second power transmission unit 122 to transmit a rotational force, the first power transmission unit 111a and the second power transmission unit 122 may be disposed at various angles other than a right angle. According to the area of the acromion to be drilled, for the convenience of drilling, the twist drill 112 may be disposed at an arbitrary angle other than a right angle with respect to the outer tube 114.

In addition, a connecting pipe 130 configured to connect the twist drill 112 and the inner tube 121 is installed in the head section 113 such that the ground bone wastes introduced through the suction port 112a is discharged to the outside through the inner tube 121. Bearings (not shown) may be additionally installed at both ends of the connecting pipe 130 not to interfere with rotational movement of the first power transmission unit 111a and the second power transmission unit 122.

As shown in FIG. 3, the inner tube assembly 120 is coupled to the outer tube assembly 110 to expose the discharge section 125 and the rotation transmission unit 123. The outer tube assembly 110 may include a coupling section 115 formed at one side of the outer circumferential surface and configured to couple a hand piece 200 connected to the discharge section 125 and the rotation transmission unit 123 to supply a rotational force to the rotation transmission unit 123 while supplying air for suctioning the ground bone wastes discharged from the discharge section 125.

As shown in FIG. 3, an insertion section 140 having a conical shape with a round end is formed at one surface of the head section 113 such that the drilling device for acromioplasty 100 according to the embodiment of the present invention can pass through the surgery area not to damage the body tissue.

Figure 4:
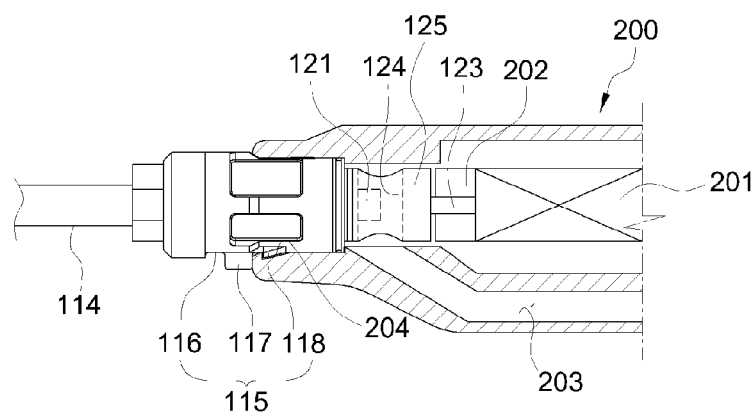
FIG. 4 is a cross-sectional view showing a coupling state of the drilling device for acromioplasty according to the embodiment of the present invention and a hand piece.

FIG. 4 is a cross-sectional view showing a coupling state between the drilling device for acromioplasty 100 according to the embodiment of the present invention and the hand piece 200.

Referring to FIG. 4, the coupling section 115 may be coupled to the hand piece 200 connected to the discharge section 125 and the rotation transmission unit 123 such that air for suctioning the ground bone waste discharged from the discharge section 125 is supplied while a rotational force is provided to the rotation transmission unit 123.

The coupling section 115 includes an elastic section 116 formed at one side of the outer circumferential surface of the outer tube assembly 110, a push section 117 disposed at a center of the elastic section 116, and a protrusion 118 protruding from an end of the elastic section 116.

The material of the elastic section 116 is not particularly limited as long as the material has an elastic property, and as another example of the elastic section 116, a spring (not shown) may be disposed at lower surfaces of the push section 117 and the protrusion 118.

As shown in FIG. 4, the drilling device for acromioplasty 100 can be securely coupled to the hand piece 200 and can be easily detached from the hand piece 200 through the coupling section 115.

The hand piece 200 includes a power unit 201 configured to provide power to rotate the inner tube assembly 120, and a suction hose 203 configured to discharge the ground bone wastes generated during the surgery to the outside. The power unit 201 includes a fastening section 202 having a groove corresponding to the rotation transmission unit 123 formed at the inner tube assembly 120, and has a groove 204 corresponding to the protrusion 118.

The ground bone wastes suctioned through the suction port 112a are discharged to the discharge port 124 through the inner tube 121, and the discharge section 125 having the discharge port 124 is connected to the suction hose 203 to discharge the ground bone wastes to the outside.

Figure 5A:
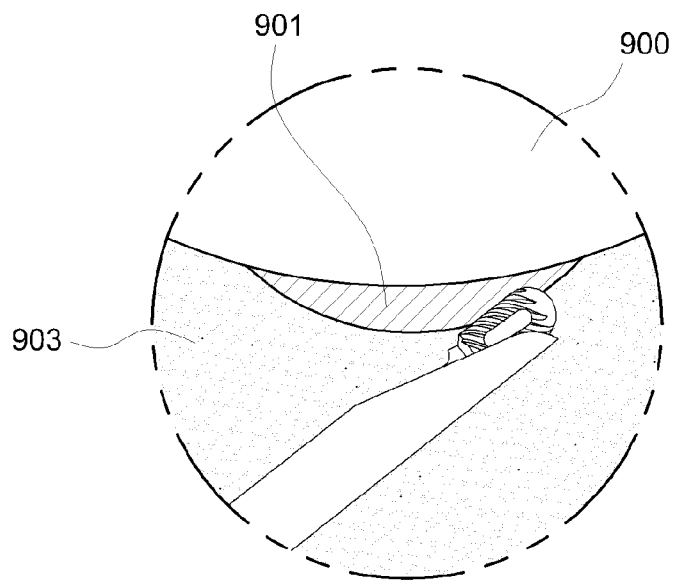
FIG. 5A is a view showing a surgery of conventional acromioplasty.
Figure 5B:
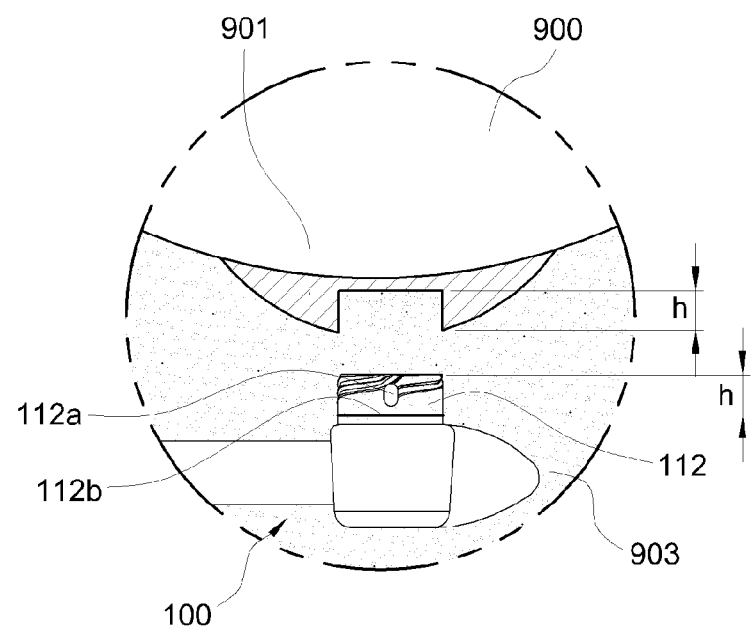
FIG. 5B is a view showing a surgery using the drilling device for acromioplasty according to the embodiment of the present invention.

FIG. 5A is a view showing a surgery of conventional acromioplasty, and FIG. 5B is a view showing a surgery using the drilling device for acromioplasty according to the embodiment of the present invention.

After the extent of which depth of bony spurs 901 should be cut is determined through radiography before the surgery, the surgery is started. However, there is no apparatus capable of determining whether the bony spurs 901 is precisely cut to the predetermined depth during the surgery, and as shown in FIG. 5A, the surgeon must find out the extent of which the depth of the bony spurs 901 is cut using his/her experience by relatively comparing the surgery area with an uncut periphery thereof. However, even a surgeon with much experience may have a cutting difference according to his/her condition or concentration during the surgery, and in particular, a surgeon with little experience cannot easily cut the spurs to the precise depth.

In order to solve the problems, as shown in FIG. 5B, the bony spurs 901 is drilled to a depth h to be cut through the surgery in reality, using the drilling device for acromioplasty according to the embodiment of the present invention, before the bony spurs 901 of the acromion is cut. Here, the gradation 112b is formed on the outer circumferential surface of the twist drill 112 such that the depth can be precisely measured. That is, as shown in FIG. 5B, when a length in which the gradation 112b is formed is h, the drilling is performed to the depth h of the bony spurs 901 to be cut by drilling the bony spurs 901 of the acromion to a position at which the gradation 112b is seen. When the acromioplasty is performed in reality, the bony spurs 901 can be precisely cut to the desired depth by cutting the bony spurs 901 until the drilled area is removed.

In addition, the suction port 112a is formed on the outer circumferential surface of the twist drill 112 such that the ground bone wastes can be discharged to the outside through the suction port 112a without floating in a body cavity 903.

As can be seen from the foregoing, the drilling device for acromioplasty according to the present invention can previously drill the acromion to a depth to be removed before the acromioplasty such that the spurs growing from the undersurface of acromion and/or the anterior undersurface of acromion can be precisely removed by the surgeon who performs the acromioplasty, and can supplement experiences to the unskillful surgeon even with little experience in acromioplasty.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A drilling device for drilling bony spurs before an acromioplasty comprising:
    an outer tube assembly including a head section that has a rotor having a first power transmission unit having a hollow structure and configured to receive power and a twist drill coupled to a lower end of the rotor with a hollow structure and provided with a suction port formed on an outer circumferential surface thereof, and an outer tube having a tubular shape and having one end to which the head section is coupled;
    an inner tube assembly including an inner tube having a hollow structure and the inner tube being rotatably inserted into the outer tube assembly, a second power transmission unit having a hollow structure and formed at one end of the inner tube, adjacent the head section, to transmit power to the first power transmission unit and being arranged in a nonparallel direction to the first power transmission unit such that the twist drill and the outer tube are disposed at a predetermined nonparallel angle, a rotation transmission unit formed at another end of the inner tube and configured to receive an external rotational force, and a discharge section disposed between the rotation transmission unit and the inner tube and including a discharge port configured to discharge ground bone wastes outside of the drilling device; and
    a connecting pipe configured to connect the suction port of the twist drill through the rotor having the first power transmission unit and through the second power transmission unit to the inner tube such that the ground bone wastes introduced through the suction port is discharged outside of the drilling device through the inner tube,
    wherein at least one gradation is formed on the outer circumferential surface of the twist drill such that a partial area of the bony spurs can be predrilled to a predetermined depth according to the at least one gradation; and
    an insertion section having a conical shape with a round end formed at one surface of the head section to cover a front tip of the head section while leaving the twist drill exposed.

2. The drilling device according to claim 1, wherein the first power transmission unit and the second power transmission unit transmit power using bevel gears.

3. The drilling device according to claim 1, wherein the inner tube assembly is coupled to the outer tube assembly to expose the discharge section and the rotation transmission unit, and
    the outer tube assembly comprises a coupling section formed on an outer circumference that is at an end of the outer tube and configured to couple a hand piece connected to the discharge section and the rotation transmission unit to supply a rotational force to the rotation transmission unit while supplying air for suctioning the ground bone wastes discharged from the discharge section.

4. The drilling device according to claim 3, wherein the coupling section comprises an elastic section formed at one side of the outer circumferential surface of the outer tube assembly, a push section disposed at a center of the elastic section, and a protrusion protruding from an end of the elastic section.

5. A method of performing an acromioplasty to remove tissue from a lower surface of an acromion, the method comprising:
    using a drilling device according to claim 1 to drill a predefined depth into bony spurs on the lower surface of the acromion; and
    performing an acromioplasty to remove tissue from the lower surface of the acromion.

* * * * *